United States Patent [19]
Lawrence et al.

[11] Patent Number: 5,955,272
[45] Date of Patent: Sep. 21, 1999

[54] DETECTION OF INDIVIDUAL GENE TRANSCRIPTION AND SPLICING

[75] Inventors: Jeanne Bentley Lawrence, Mapleville, R.I.; Carol Villnave Johnson, Stowe; Yigong Xing, Northborough, both of Mass.

[73] Assignee: University of Massachusetts, Boston, Mass.

[21] Appl. No.: 08/682,924

[22] Filed: Jul. 16, 1996

Related U.S. Application Data

[63] Continuation-in-part of application No. 08/023,953, Feb. 26, 1993, Pat. No. 5,563,033.

[51] Int. Cl.$^6$ .................................................. C12Q 1/68
[52] U.S. Cl. .................... 435/6; 435/69.3; 435/91.1; 435/810; 436/501; 536/23.1; 536/24.1; 536/24.3; 536/24.31; 536/24.32; 536/24.33; 935/77; 935/78
[58] Field of Search ........................ 435/6, 69.3, 810, 435/91.1; 436/501; 536/23.1, 24.1, 24.3–24.33; 935/77, 78

[56] References Cited

U.S. PATENT DOCUMENTS

| | | | |
|---|---|---|---|
| 4,888,278 | 12/1989 | Singer et al. | 435/6 |
| 5,563,033 | 10/1996 | Lawrence et al. | 435/6 |

FOREIGN PATENT DOCUMENTS 0 612 851 A1  8/1994  European Pat. Off. .

OTHER PUBLICATIONS

Xing et al., *J. Cell Biol.* 131:1635–1647 (1995).
Xing et al., *Science,* 259:1326–1330 (1993).
Carter et al., *Science,* 259:1330–1335 (1993).
Xing et al., *Trends in Cell Biol.* 3:346–352 (1993).
Xing et al., *J. Cell Biology,* 115:372A, Abstract No. 2162 (1991).
Lawrence et al., *Cell,* 57:493–502 (1989).
Carter et al., *J. Cell Biology,* 115:1191–1202 (1991).
Raap et al., *Exptl. Cell Res.* 197:319–322 (1991).
Xing et al., *J. Cell Biol.* 112:1055–1063 (1991).
Nevins, *Ann. Rev. Biochem* 52:441–466 (1983).
Lawrence et al., *Proc. Natl. Acad. Sci. USA,* 87:5420–5424 (1990).
Chelly et al., *Nature* 333:858–860 (1988).

*Primary Examiner*—Ardin H. Marschel
*Attorney, Agent, or Firm*—Fish & Richardson, P.C.

[57] ABSTRACT

Disclosed are in situ hybridization methods for differentially detecting an RNA and the gene from which it was transcribed, while preserving the spatial relationship of the RNA transcript and the gene. Also disclosed are in situ hybridization methods for simultaneously detecting two alleles of the same gene in a single cell, while differentially detecting RNA transcribed each of the two alleles. Also disclosed are in situ hybridization methods for detecting normal and defective RNA splicing.

16 Claims, 2 Drawing Sheets

DETECTION OF INDIVIDUAL GENE TRANSCRIPTION AND SPLICING

This application is a continuation-in-part of U.S. Ser. No. 08/023,953, filed Feb. 26, 1993, now U.S. Pat. No. 5,563,033.

FIELD OF THE INVENTION

The present invention relates to cell biology, molecular genetics and in situ hybridization.

BACKGROUND OF THE INVENTION

The site of RNA processing and the spatial relationship between RNA processing and transcription in mammalian nuclei is a subject of a long-standing interest in cell biology. There is evidence for and against the cotranscriptional splicing of precursor mRNAs. A. L. Beyer and Y. N. Osheim (*Semm. Cell Biol.* 2:131 (1991)) have shown that nascent transcripts in Drosophila are associated with spliceosomes, and in some cases, the spliceosome and nascent transcripts can be directly visualized by electron microscopy. In contrast, J. R. Nevins (*Annu. Rev. Biochem.* 52:441 (1983)) and others have shown that the unspliced transcripts in mammalian cells can be isolated in the poly(A) fraction, indicating that splicing is posttranscriptional.

Prior art studies on whether or not mRNA transcripts in mammalian cells are localized at the site of transcription or are free to diffuse within the nucleus after synthesis have yielded inconsistent results. Those studies that have reported localized foci of RNAs have failed to establish the significance of such localizations. Highly localized nuclear "tracks" of specific viral mRNAs have been observed by fluorescence microscopy in chromatin-depleted nuclear matrix extracts (J. B. Lawrence, R. H. Singer and L. M. Marselle. *Cell* 57:493 (1989); Y. Xing and J. B. Lawrence. *J. Cell Biol.* 112:1055 (1991)). Several viral RNAs have been observed to localize at only one or two sites within the nucleus (J. B. Lawrence, et al. (1989). supra; J. B. Lawrence, L. M. Marselle, K. S. Byron, J. L. Sullivan and R. H. Singer. *Proc. Natl. Acad. Sci. USA* 87: 5420 (1990); A. Raap et al. *Exp. Cell Res.* 197:319 (1991)), but this observation is in contrast to microinjected globin RNA, which appears to diffuse within the nucleus. Lawrence, et al. (1990) have speculated that these tracks might represent sites of transcription, but have not ruled out other functions e.g., sites of RNA processing, RNA transport, or some other cellular function. Moreover, they did not spatially correlate the foci with any particular active genes.

Total nuclear polyadenylate RNA (poly(A) RNA) has been shown to accumulate in 20 to 50 discrete "transcript domains" which coincide with the location of small nuclear ribonucleoproteins (snRNPS) (K. C. Carter, K. L. Taneja and J. B. Lawrence. *J. Cell Biol.* 115:1191 (1991)). These snRNPs have previously been reported to exhibit a clustered nuclear distribution coincident with the spliceosome assembly factor SC-35. Although the association of poly(A) RNA with snRNPs in these studies was observed using hybridization of probes to DNA and mRNA in the same cell, it was not possible to make any conclusions concerning spatial correlation of transcription and processing of a specific RNA with expression of a specific gene because the DNA-specific probe was directed to untranscribed centromere DNA and the mRNA-specific probe oligo(dT) hybridized to total mRNA.

SUMMARY OF THE INVENTION

We have discovered methods for differentially detecting an RNA and the gene from which it was transcribed, while preserving the spatial relationship of the RNA transcript and the gene. We have also discovered methods for simultaneously detecting two alleles of the same gene in a single cell, while differentially detecting RNA transcribed from each of the two alleles. In addition, we have discovered in situ hybridization methods for detecting normal RNA splicing, defective RNA splicing, and alternative RNA splicing. Based on these discoveries, the invention has various aspects featuring different in situ hybridization methods for detecting normal or defective splicing of RNA in a cell.

In a first aspect, the invention features a method for detecting normal RNA splicing in a cell. The method includes the steps of: (a) fixing the cell with a fixative such that the nucleus remains penetrable by labeled probes, and the nucleic acids are preserved in place; (b) hybridizing the fixed cell with an intron-specific nucleic acid probe able to hybridize to an intron of interest encoded by a gene of interest, the intron-specific probe bearing a first label; (c) hybridizing the fixed cell with an exon-specific nucleic acid probe able to hybridize to at least one exon in said gene of interest, said exon-specific probe bearing a second label, said second label being distinguishable from the first label; (d) detecting the second label as a large focus or track; (e) detecting the first label as a small focus or track within the large focus or track, the small focus or track having a size and shape such that it does not substantially totally overlap the large focus or track, as an indication of normal RNA splicing in the cell.

In a second aspect, the invention features a first method for detecting defective splicing of a particular intron, if present, in a cell. The method includes the steps of: (a) fixing the cell with a fixative such that the nucleus remains penetrable by labeled probes, and the nucleic acids are preserved in place; (b) hybridizing the fixed cell with an intron-specific nucleic acid probe able to hybridize to an intron of interest encoded by a gene of interest, the intron-specific probe bearing a detectable label; (c) detecting the label as a large focus, as an indication of the presence of defective splicing of RNA transcribed from the gene of interest in the cell.

In third aspect, the invention features a second method for detecting defective splicing at a particular intron, if present, in a cell. The method includes the steps of: (a) fixing the cell with a fixative such that the nucleus remains penetrable by labeled probes, and the nucleic acids are preserved in place; (b) hybridizing the fixed cell with an intron-specific nucleic acid probe able to hybridize to an intron of interest encoded by a gene of interest, the intron-specific probe bearing a first label; (c) hybridizing the fixed cell with an exon-specific nucleic acid probe able to hybridize to at least one exon in the gene of interest, the exon-specific probe bearing a second label, the second label being distinguishable from the first label; (d) detecting the first label as a signal focus that substantially completely overlaps a signal focus from the second label, as an indication of defective splicing of RNA transcribed from the gene of interest in the cell, if defective splicing is present. Although steps (b) and (c) can be carried out sequentially, they can also be carried out simultaneously, by having the intron-specific probe and the exon-specific probe present in a single hybridization reaction.

In fourth aspect, the invention features a first method for generally detecting, i.e., regardless of intron involved, defective RNA splicing in a cell, if present. The method includes the steps of: (a) fixing the cell with a fixative such that the nucleus remains penetrable by labeled probes, and the nucleic acids are preserved in place; (b) subjecting the fixed cell to a single in situ hybridization reaction that includes: (1) a labeled, full-length genomic probe comprising the antisense sequence of an entire gene of interest, the full-length genomic probe bearing a label, and the full-length genomic probe being present in the hybridization reaction at a concentration between 0.2 μg/ml and 20 μg/ml; and (2) an unlabeled full-length cDNA probe comprising the complete coding region of the gene of interest, the cDNA probe being present in said hybridization reaction at a concentration from 50-fold greater to 500-fold greater than the concentration of the labeled genomic probe; and (c) detecting the label as a large focus in the nucleus of said cell, as an indication of defective splicing in RNA transcribed from the gene of interest in the cell.

In a fifth aspect, the invention features a second method for generally detecting, i.e., regardless of intron involved, a defectively spliced RNA in a cell, if present. The method includes the steps of: (a) fixing the cell with a fixative such that the nucleus remains penetrable by labeled probes, and the nucleic acids are preserved in place; (b) hybridizing the fixed cell with a cDNA bearing a first label; (c) fixing the cell to preserve in place the hybridized cDNA of step (b); (d) hybridizing the fixed cell with a full-length genomic probe comprising the antisense sequence of an entire gene of interest, the full-length genomic probe bearing a second label, the second label being distinguishable from said first label; and (e) detecting the second label as a focus that substantially completely overlaps a signal focus from said first label, as an indication of defective splicing of RNA transcribed from the gene of interest in the cell.

As used herein, "associated with a selected gene" means spatially correlated with a part of the coding or noncoding regions of the gene, or a sequence linked to the gene sufficiently closely to serve as an effective marker for the location of the gene.

As used herein, "DNA specific probe" means a probe that hybridizes to a DNA target sequence without substantial hybridization to DNA non-target sequences, RNA non-target sequences, or RNA target sequences.

As used herein, "RNA-specific probe" means a probe that hybridizes to an RNA target sequence without substantial hybridization to RNA non-target sequences. Substantial hybridization to DNA sequences in the gene encoding the RNA target sequence is prevented by carrying out the hybridization reaction under non-denaturing conditions, i.e., conditions wherein genomic DNA remains double-stranded.

As used herein, "large focus" means, with regard to a particular cell type, genetic locus, and in situ hybridization protocol, an RNA hybridization-dependent signal focus whose size and shape are substantially similar to those of an RNA-hybridization-dependent signal focus produced by a labeled cDNA probe.

As used herein, "substantial hybridization" to non-target nucleic acid sequences is a level of hybridization that results in a spurious signal level sufficient to obscure or confuse detection of signals from the target nucleic acids.

As used herein, "simultaneous hybridization" means an in situ hybridization process in which a first probe and an second probe provide separately distinguishable signals, regardless of whether the process includes cohybridization of DNA or RNA to specific probes in a single reaction step or, alternatively, sequential hybridization to the first probe followed by hybridization to the second probe.

Unless otherwise defined, all technical and scientific terms used herein have the same meaning as commonly understood by one of ordinary skill in the art to which this invention pertains. In case of conflict, the present application or patent, including definitions, will control.

All publications, patent applications, patents, and other references mentioned herein are incorporated by reference in their entirety. In particular, the figures of any patent issuing on U.S. application Ser. No. 08/023,953 are incorporated by reference.

Although methods and materials similar or equivalent to those described herein can be used in the practice or testing of the present invention, the preferred methods and materials are described below. The following description of materials, methods and examples are illustrative only and not intended to be limiting. Various features and advantages of the invention will be apparent from the following detailed description, and from the claims.

BRIEF DESCRIPTION OF THE DRAWINGS

The file of this patent contains at least one drawing executed in color. Copies of this patent with color drawings will be provided by the Patent and Trademark Office upon request and payment of the necessary fee.

DETAILED DESCRIPTION

The present invention provides improved in situ hybridization methods, including refinements in cell permeabilization and cell fixation. By virtue of these improved in situ hybridization methods, labile nuclear RNAs are preserved in place, and signals from RNA-specific probes hybridized to their RNA targets are preserved during simultaneous or subsequent in situ hybridization of DNA-specific probes to their DNA targets. Conventional filter hybridization and in situ hybridization targeting cytoplasmic RNA are generally incapable of distinguishing allelic variants. Genetic mutations that do not affect an mRNA enough to be detectable by conventional nucleic acid hybridization can nevertheless affect the distribution, processing, or expression level of the RNA. Such abnormalities can be detected by the methods of the present invention.

The present invention provides simultaneous in situ hybridization detection of an active gene, and the RNA transcribed from it, in a cell nucleus. This make it possible to determine which copies of a gene in the nucleus are being expressed and what their relative expression levels are. As a result, the invention allows comparison of the expression of maternal and paternal alleles, in a single cell (gene imprinting).

By providing information on the intracellular distribution of a specific viral RNA, the present invention allows determination of whether a viral infection is latent or productive. For example, using in situ hybridization to detect EBV-specific RNA, we have demonstrated that the nucleus of a cell latently infected with a single integrated copy of the virus displays a single, elongated RNA track present in the nucleus only. In contrast, a productive infection results in RNA-specific signals in both the nucleus and cytoplasm.

The present invention preserves target RNA in place in the nucleus. Therefore, nonabundant, labile mRNAs previously undetectable in the cytoplasm can be detected in the nucleus, in highly localized foci or tracks. Such preservation of RNA concentration at a given nuclear site effectively increases RNA detection sensitivity. An example of a very low abundance RNA detected by methods of the present invention, but not by prior art in situ hybridization methods, is dystrophin mRNA (0.01% of mRNA; J. Chelly, J. C. Kaplan, P. Maire, S. Gautron and A. Kahn Nature 333:858 (1988)).

The present invention can be used to assess a transgene's expression level. This is advantageous because transgenes are often not expressed at normal levels and expression levels are often dependent on the site of integration.

In addition to providing information on the nuclear transcription site, transcription level, and distribution of a specific RNA, the present invention can be used to provide information on processing of a specific RNA. With proper design of RNA-specific probes, the present invention can be used to detect defective RNA splicing or alternative RNA splicing. Principles and procedures for using the present invention to obtain information on RNA processing are described herein primarily in terms of detecting defective RNA splicing. One of ordinary skill in the art will recognize, however, that essentially the same procedures can be used to detect alternative RNA splicing.

Some genetic diseases, e.g., Duchenne's muscular dystrophy and cystic fibrosis, appear to be caused by defective RNA splicing. The present invention is useful for diagnosing diseases resulting from defective RNA splicing. Some diseases, e.g., some forms of colon cancer, appear to result from alternative RNA splicing. The present invention is useful for diagnosing diseases resulting from alternative RNA splicing.

The simultaneous hybridization methods of the present invention employ at least two nucleotide probes with covalently attached detectable labels. Preferably, the probes are fluorescently labeled. The present invention includes embodiments that use a DNA-specific probe and an RNA-specific probe, and embodiments that use two different RNA-specific probes.

DNA-Specific Probe

A DNA-specific probe can be designed so as to hybridize only to the transcribed strand of the DNA in the coding region of the gene, thereby preventing non-specific hybridization to the mRNA transcript. Alternatively, the DNA-specific probe can be complementary to a 5' or 3' untranscribed sequence of the target gene, or some other closely linked, but untranscribed, sequence. Sequences separated from the gene or RNA track by as much as approximately 3 megabases (about 2 $\mu$m) can be used, because they can appear close to the RNA signal due to packaging of the chromatin. It was not previously recognized that such distant sequences could be useful for marking or identifying a site of RNA transcription, and they have not previously been used in this manner.

RNA Specific Probe

The RNA-specific probe is designed to hybridize to the RNA transcript of the selected gene without substantial hybridization to non-targeted DNA or RNA sequences. This specificity results from the hybridization protocol, because the probe would otherwise hybridize to the DNA strand from which the RNA was transcribed. This RNA-specificity enables the invention to distinguish between a gene and its transcript. The RNA-specific probe can be complementary to the genomic sequence of the transcribed portion of the selected gene or from the corresponding cDNA. If processing or distribution of the target RNA is being analyzed, intron-specific and exon-specific probes may be used to localize processed and unprocessed transcripts or to assess the extent of RNA processing.

Probe Length

For minimization of spurious background signals, the probe size range is critical for non-radioactively labeled probes, not the average fragment size. If a sufficient proportion of the nucleotides in the probe composition exceed a maximum critical length, background is significantly increased relative to the specific signal and sensitivity is reduced. When indirectly non-radioactively labeled probes are used in the present invention, they preferably comprise nucleotide fragments essentially all of which are less than about 1,000 nucleotides in length after labeling, and more preferably less than about 200 nucleotides in length, after labeling. If the probe preparations are produced by nick translation (which produces a broad range of probe lengths), they are preferably subject to a size selection step prior to use to exclude substantially all probes larger than about 1,000 nucleotides. Chemically synthesized oligonucleotide probes are also preferably synthesized according to these size criteria.

Probe Concentration

For optimum sensitivity, the probes are preferably used in hybridizations at a relatively high concentration (about 100 times the amount of expected available RNA) to drive the kinetics of the reaction toward hybridization. In general, this will be a probe concentration of from about 0.2 μg/ml to about 20.0 μg/ml, preferably about 2.0 μg/ml. Control of probe size allows the probe concentration to be increased without increasing background, thereby providing more efficient hybridization kinetics.

Probe Label

The labels attached to the DNA-specific probe and the RNA-specific probe are separately detectable. This allows differentiation between the probe hybridized to the DNA target sequence and the probe hybridized to the corresponding RNA target. Preferably, the label on the DNA-specific probe and the label on the RNA-specific probe are different fluorescent moieties whose emission wavelengths, i.e., colors, are clearly distinguishable. A preferred pair of fluorescent labels is rhodamine (red) and fluorescein isothiocyanate ("FITC"; green). The invention is not limited to detection of a single gene/transcript pair using two colors of fluorescence. The use of additional specific probes with labels emitting light of additional distinguishable colors allows simultaneous detection of additional nucleic acid target sequences.

The label can be attached to the nucleotide probe using any of various methods known in the art, e.g., during chemical synthesis or nick translation of a cloned fragment. See, e.g., U.S. Pat. No. 4,711,955; C. Kessler, et al. *Biol. Chem.* Hoppe-Seyler 371:917 (1990). In a preferred embodiment, the fluorescent label is attached to the probe via a ligand-derivatized deoxyribonucleoside triphosphate (dNTP) incorporated into the probe during probe synthesis. The ligand binds specifically to a receptor to which the detectable label is covalently attached. Preferred ligands are digoxigenin and biotin. Either of those ligands can be linked to a dNTP, for incorporation into an oligonucleotide probe, according to conventional methods.

Alternatively, the detectable label, e.g., a fluorochrome, can be covalently attached to the oligonucleotide probe. This can be done by carrying out conventional oligonucleotide synthesis using a modified base at each position in the nucleotide sequence where a label is desired. The modified base provides a functional group through which the label is covalently attached to the oligonucleotide in a subsequent step. In such an embodiment, the functional group is preferably an amino group. Preferably, the functional group is at the end of a spacer arm. For preparation of amino modified bases, see, e.g., Jablonski et al., *Nucleic Acids Res.* 14:6115–6128 (1986); and Ruth, *DNA* 3:123 (1984). A preferred modified base is a deoxythimidine analog commercially available as "Amino-Modifier C6 dT" (Glen Research, Sterling, Va.). During synthesis of an oligonucleotide, the functional group on the modified base (for attachment of the label) typically bears a protecting (blocking group), e.g., a trifluoroacetamide group. One of ordinary skill in the art will recognize that the protecting group must be removed by a suitable chemical reaction before the functional group can be used for attachment of the label.

Sample Preparation

Cells prepared according to the present invention remain morphologically intact. Because nuclear mRNAs are generally very labile, it was unexpected that hybridization of an RNA-specific probe to RNA could be followed by denaturation and specific hybridization to DNA without loss of the RNA signal.

Although the following description is directed to analysis of cells, it will be apparent to those skilled in the art that tissue samples may be substituted for cells and analyzed accordingly.

For most cell types, initial treatment to permeabilize the nuclear membrane is required to obtain penetration of the probe. An important feature of the invention is therefore the discovery of methods for permeabilizing the nucleus prior to hybridization which preserve the nuclear RNA. These procedures may sacrifice the cytoplasmic RNA. A few cell types which are small and have minimal amounts of cytoplasm, such as lymphocytes and the rat PC-12 cells described below, do not require such treatment prior to hybridization.

For permeabilization the cells may be placed in any buffer suitable for maintaining the integrity of the cells. However, the preferred buffer is cytoskeleton buffer described by E. G. Fey, G. Krochmalino and S. Penman. *J. Biol. Chem.* 102:1654 (1986) previously used for isolation of nuclear ribonucleoprotein matrix, with addition of an RNAse inhibitor. Permeabilization is preferably achieved by treatment of the cells for 10 seconds to 10 minutes, at 4° C., with a nonionic biological detergent such as NONIDET™ P-40 (an octylphenol-ethylene oxide) or TRITON™ (a polyoxyethylene ether). Most preferably, the treatment time is approximately 3 minutes, and the nonionic biological detergent is TRITON-X 100.

Permeabilization releases RNases that can degrade the target RNA. Therefore, the detergent treatment and subsequent steps include an RNase inhibitor, e.g., vanadyl sulfate complex or RNAsin. To further reduce degradation by RNases, the cells are kept cold prior to fixation. The RNase inhibitor is also added to antibodies and detection reagents that could contain RNase, e.g., anti-digoxigenin. The permeabilized cells are then fixed for about 1–15 min. with a fixative, usually in a buffer such as phosphate buffered saline (PBS). The fixative is selected such that the fixed cells remain penetrable by the probe and the nucleic acids are preserved and retained within the membrane. These fixatives restrict cross-linking and/or precipitation of proteins within the cell so that the matrix is less "hardened" to probe penetration but do not induce autofluorescence. In general suitable fixatives are as described in U.S. Pat. No. 4,888,278 and J. B. Lawrence, et al. (1989) supra. A preferred fixative with these properties is paraformaldehyde, which is used at about 1–10% in PBS for about 5–30 minutes, preferably 5–15 min., to fix the permeabilized cells. The most preferred fixing conditions are about 4% paraformaldehyde for about 5 min. at room temperature.

These treatments allow the cells to be permeabilized and fixed without destruction or substantial diffusion of targeted nuclear RNA, although cytoplasmic RNA may be lost. If desired, the cells may then be stored in 70% ethanol at 4° C. until hybridization. Storage may improve the results of the hybridization in certain cases, provided the cells are not stored for more than a few months.

Sequential Hybridization Involving DNA-Specific and RNA-Specific Probes

In one method for simultaneously detecting a gene and its transcripts, RNA-specific and DNA-specific probes are hybridized with cells sequentially. The sequential hybridization is most suitable for situations in which the target nucleic acid sequence is the same in both the RNA and the DNA or if the RNA target is particularly fragile (sequential hybridization reduces exposure of the RNA to harsh reaction conditions as compared to cohybridization). The RNA of the cells is hybridized first to the RNA-specific probe under non-denaturing conditions so that the DNA is not available for hybridization. This is preferably accomplished by providing hybridization conditions in which the DNA is not denatured (i.e., it remains double stranded) and is therefore unavailable for hybridization to the single stranded probe. Because the RNA is already single stranded, the RNA-specific probe hybridizes to the RNA.

Non-denaturing conditions are preferably accomplished by adjusting (lowering) the concentration of formamide in the hybridization buffer and avoiding elevated temperatures. Typically, the formamide concentration will be less than about 60% more preferably about 50% in 2× saline sodium citrate buffer (SSC). The RNA-specific probe will generally be hybridized to the nucleic acid of the fixed cells for about 10 min.–20 hr., more preferably for about 2–16 hr., and most preferably for about 3–4 hr. at 37° C. If additional reagents are required to visualize the signal, as when the probe contains a hapten detectable by addition of a receptor conjugated to a label, they are then added to the hybridized cells under appropriate conditions to produce the detectable signal indicative of probe hybridization to RNA.

In some cases, a diffuse RNA signal is produced which is not due to hybridization of the RNA-specific probe to target sequences. Addition of $C_{o t}1$ DNA to the RNA-specific hybridization reaction eliminates or reduces this diffuse signal, which is believed to be due to the presence of repetitive elements in some RNAs that hybridize to certain probes. This allows the localized sites of specific RNA, correlating to gene expression, to be visualized.

Following hybridization of the RNA-specific probe to the RNA of the fixed cells, the cells are fixed a second time. This second fixing step preserves and stabilizes the signal from the RNA-specific probe during subsequent denaturation and hybridization of the DNA-specific probe. This step is important for maintaining the RNA signal at the site of transcription and preventing loss of signal at that site either by degradation, diffusion or some other mechanism. The second fixative is preferably paraformaldehyde. The cells are preferably treated with about 1–10% paraformaldehyde for about 5–30 min. The most preferred conditions for the second fixation are 4% paraformaldehyde for 10–15 min. at room temperature.

The double stranded DNA in the cells is then denatured prior to hybridization with the DNA-specific probe. Preferably, denaturation is accomplished by treatment with about 60–80% formamide at elevated temperature, more preferably about 70% formamide in 2× SSC at about 70° C. for about 2 min. The DNA-specific probe is then hybridized to the denatured nucleic acids of the cell for about 10 min. to 20 hr., more preferably about 2–16 hr. at 37° C. The DNA-specific signal is then developed by conventional methods.

Sequential Hybridization Involving Separately Labeled Probes with Same Nucleotide Sequence In an alternative method for simultaneously detecting a gene and its transcripts, the same nucleotide sequence is used in a first probe and a second probe, with separately detectable labels. Through completion of the second fixation step, the steps are the same as in the sequential hybridization with DNA-specific and RNA-specific probes (above)—except that the first probe is used instead of the RNA-specific probe.

After the second fixation step, the double stranded DNA is denatured, and the RNA in the cells is hydrolyzed prior to hybridization of the denatured DNA with the second probe. Preferably, denaturation is accomplished by treatment with sodium hydroxide in 70% ethanol, for 4–5 minutes. The sodium hydroxide concentration preferably is from 0.01 M to 0.2 M, and more preferably it is about 0.07 M. The cells are then dehydrated through ethanol treatment. The second probe is then hybridized with the denatured DNA in the cell for about 10 min. to 20 hr., more preferably about 2–16 hr. at 37° C. The DNA-specific signal is then developed by conventional methods.

Simultaneous DNA and RNA Hybridization

In a second embodiment, hybridization to DNA and RNA targets is performed simultaneously in a single hybridization reaction (cohybridization) under DNA-denaturing conditions. This embodiment reduces the number of steps and is useful when different sequences are being targeted in the DNA and RNA. Although it may weaken the RNA signal, if the target RNA is abundant, some loss of signal can be tolerated.

The simultaneous cohybridization protocol is essentially the RNA hybridization portion of the sequential hybridization protocol, but with denaturing conditions. The probes are added simultaneously to the permeabilized, fixed cells in which the nucleic acids have been denatured by treatment with 60–80% formamide, preferably 70% formamide, at about 70° C., for 2 minutes. After hybridization at about 37° C. for about 2 hr. to overnight, both probe signals are developed. $C_{o t}1$ DNa may be added to the hybridization to reduce diffuse signals from repetitive sequences if necessary.

The simultaneous hybridization methods of the present invention allow identification of the function of the previously observed RNA tracks as sites of transcription and processing. The methods fix the RNA at the site of transcription so that a specific mRNA can be spatially correlated with the gene from which it is transcribed.

The results of sequential or simultaneous RNA/DNA hybridization procedures according to this invention can be interpreted and analyzed qualitatively, semi-quantitatively or quantitatively. The methods are useful for determining whether or not expression of a selected gene is occurring simply by observing the presence or absence of RNA tracks or foci. That is, the number and location of distinct foci or tracks of RNA can be used to determine the number and/or location of copies of a selected gene which are actively being expressed. Alternatively, using instrumentation or subjective methods of data analysis, the level of RNA fluorescence associated with expression of a selected gene can be used to quantify the amount of mRNA which is being transcribed relative to another gene or relative to a predetermined level of expression. For example, computerized digital image microscopy or densitometry of standard photographs as is known in the art are useful methods for quantitating fluorescence. Such quantitative and semi-quantitative analysis of the data is useful for determining over-expression or under-expression of a selected gene. Results obtained using transgenes suggest that a two-fold difference in gene expression is subjectively detectable, for example, by visual analysis of fluorescence levels directly in the microscope or on photographs.

Detection of Defective Splicing at a Particular Intron

In a third embodiment, the present invention can be used to detect defective RNA splicing with respect to a particular intron in RNA transcribed from a gene of interest, when the nucleotide sequence of the intron is known. In a single cell, normally spliced RNA (transcribed from a normal allele of a gene of interest), if present, can be visually distinguished from defectively spliced RNA, if present (transcribed from a mutant allele of a gene of interest). In such embodiments, in situ hybridization is carried out with two differently labeled probes: an exon-specific probe and an intron-specific probe. Hybridization with the two probes can be carried out simultaneously or sequentially.

Defectively spliced RNA transcribed from a mutant allele and normally-spliced RNA transcribed from a corresponding normal allele are distinguished according to: (a) size and/or intensity of the signal foci, when an intron-specific probe is used alone; or (b) the spatial distribution of intron-specific probe signal foci, relative to cDNA probe foci, when an intron-specific probe and a cDNA probe are used together.

Figure 1A:
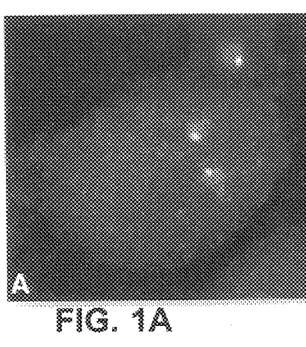
FIG. 1A is a digitized color photomicrograph of WI-38 control cells simultaneously hybridized with probes specific for collagen Iα1 intron 26 (red) and collagen Iα1 cDNA (green). Regions of overlap appear yellow. The insets show examples of signals from other cells, where the regions of overlap occupy only a portion of the focus formed by the cDNA signals.
Figure 1B:
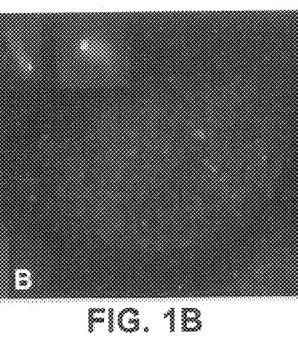
FIG. 1B is a digitized color photomicrograph of the same cell in FIG. 1A, wherein only the signal from the intron-specific probe is shown.
Figure 1C:
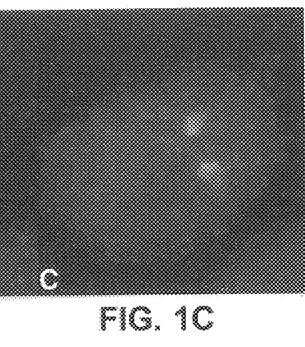
FIG. 1C is a digitized color photomicrograph of the same cell in FIGS. 1A and 1B, wherein only the signal from the cDNA-specific probe is shown.
Figure 1D:
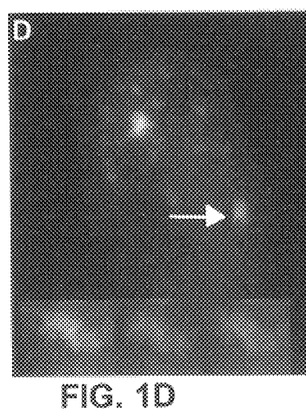
FIG. 1D is a digitized color photomicrograph of 054 cells from a heterozygotic patient with osteogenesis imperfecta type 1, simultaneously hybridized with a probe specific for collagen Iα1 intron 26 (red) and collagen Iα1 cDNA (green). Regions of overlap appear yellow. This image illustrates the differing extent of overlap between the intron 26 signal and the cDNA signal at the two different alleles, i.e., upper focus and lower focus (arrow). Triple inset shows examples of signal foci from other cells; signals from both probes (left); intron-specific signal (center); cDNA signal (right).
Figure 1E:
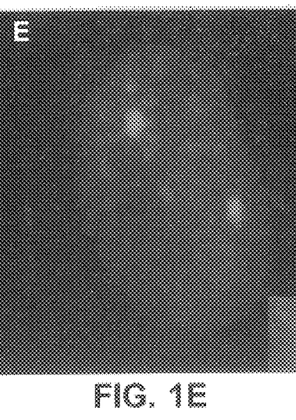
FIG. 1E is a digitized color photomicrograph of the same cell in FIG. 1D, wherein only the signal from the cDNA specific probe is shown.
Figure 1F:
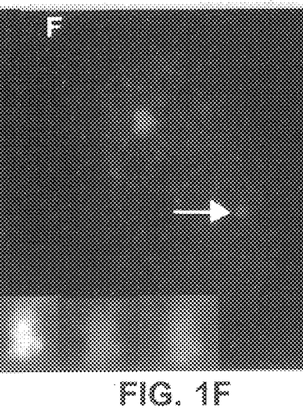
FIG. 1F is a digitized color photomicrograph of the same cell in FIGS. 1D and 1E, wherein only the signal from the intron-specific probe is shown. This image illustrates the differences in size and intensity of the signal foci at the two different alleles, when an intron-specific probe is used. The greater size and intensity of the upper focus reflects defective splicing of RNA transcribed at that allele. Triple inset shows examples of signal foci from other cells; signals from both probes (left); intron-specific signal (center); cDNA signal (right).

The signal from an intron-specific probe hybridized to RNA transcribed from a normal allele generally appear as a small focus at the periphery of a larger focus produced by the signals from an exon-specific probe (FIGS. 1A–1C). This suggests that the normal splicing events take place rapidly after transcription, so that the RNA does not have time to travel far before its introns are removed by normal splicing reactions. In contrast, the signal from an intron-specific probe hybridized to defectively spliced RNA transcribed from a mutant allele typically appears as a large focus that substantially completely overlaps the signal from the exon-specific probe (FIGS. 1D–1F). This indicates that normal splicing reactions are not occurring, and that at least a portion of the intron of interest is not being removed from the RNA.

Probes designed with a length and sequence such that they detectably hybridize only at an intact intron-exon junction ("junction-specific probes") are known. A junction-specific probe contains a portion complementary to the intron side of a junction, and an adjacent portion complementary to the exon side of the junction. In a junction-specific probe, neither portion alone is long enough to yield detectable hybridization. Detectable hybridization requires the simultaneous participation of both portions—which occurs only at an intron-exon junction. In the context of the present invention, a junction specific probe can is "intron-specific," because by definition, a junction requires the presence of an intron sequence.

General Detection of Defective Splicing in a Gene of Interest

Figure 2A:
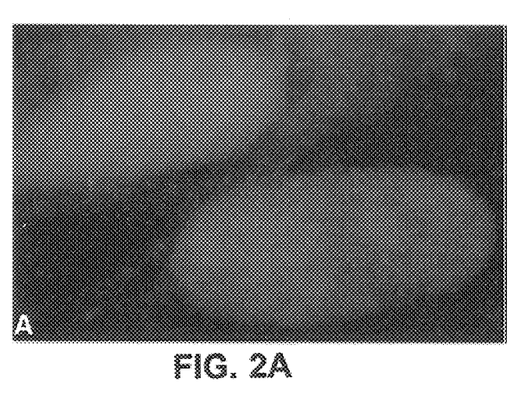
FIG. 2A is a digitized color photomicrograph of a WI-38 cell following hybridization of a biotin labeled collagen cDNA probe in the presence of excess unlabeled full-length collagen cDNA. Collagen Iα1 RNA is not detectable.
Figure 2B:
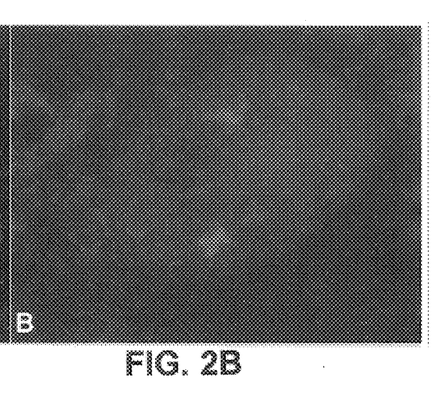
FIG. 2B is a digitized color photomicrograph of a WI-38 cell following hybridization of a biotin labeled collagen cDNA probe in the absence of an unlabeled competitor.
Figure 2C:
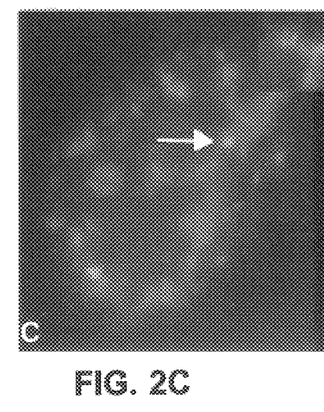
FIG. 2C is a digitized color photomicrograph of a WI-38 cell following hybridization of a digoxigenin labeled full-length collagen genomic probe (red) in the presence of excess unlabeled full-length collagen cDNA. SC-35 domains are shown in green. The collagen genomic probe signals colocalize with the edges of the SC-35 domains. Each triple inset shows, in other cells, colocalization of genomic probe signal and SC-35 domains (left), collagen genomic probe signal only (center), and SC-35 domains only (right).
Figure 2D:
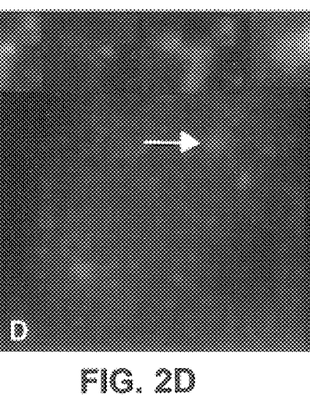
FIG. 2D is a digitized color photomicrograph of the same cell in FIG. 2C, wherein only the signal from the digoxigenin labeled full-length collagen genomic probe is shown.
Figure 2E:
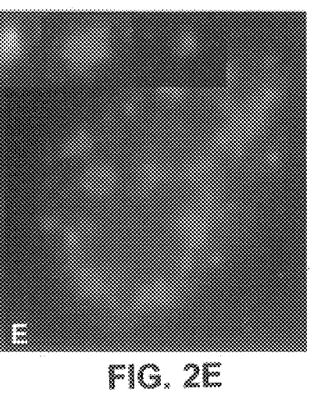
FIG. 2E is a digitized color photomicrograph of the same cell in FIG. 2C, wherein only the signal from the SC-35 domains is shown.

In a fourth type of embodiment, called "exon suppression" hybridization, the present invention can be used for general detection of a splicing defect anywhere in a gene of interest, even in the absence of information about any particular intron. One exon suppression embodiment involves simultaneous in situ hybridization using a labeled, full-length genomic probe for the gene of interest, and an unlabeled full-length cDNA probe for that gene. The labeled genomic DNA probe is present in a conventional concentration for in situ hybridization, and the unlabeled cDNA is present in excess. Preferably, the unlabeled cDNA is present in 50-fold to 500-fold greater concentration than the labeled genomic DNA probe. Any intron, or substantial portion of an intron, remaining in RNA transcribed from the gene of interest will be detected with the labeled genomic probe. Any defectively spliced intron will appear as a large focus, or as a focus of relatively greater intensity. Although the labeled genomic probe contains all of the exons, it is outcompeted by the unlabeled cDNA, which is present in excess (FIGS. 2A–2B). Any potential signals resulting from hybridization of the labeled genomic probe with exons are "suppressed" by the unlabeled cDNA. Therefore, the genomic probe is rendered—in effect—specific for any and all introns in the gene of interest (FIGS. 2C–2E).

Another "exon suppression" embodiment of the invention involves sequential hybridization. A first in situ hybridization is done using a labeled cDNA probe for the gene of interest, followed by a fixation step to retain the cDNA signal. A second in situ hybridization is done on the same sample using a labeled full-length genomic probe (which contains all introns) whose label is distinguishable from the label on the cDNA probe, in the presence of an excess concentration of unlabeled full length cDNA probe. Preferably, the two distinguishable labels are differently colored fluorophores.

The following experimental examples are presented to illustrate certain embodiments of the invention and are not to be construed as limiting the invention as defined by the appended claims.

EXAMPLE 1

Fibronectin RNA Detected with Intron-Specific and Exon-Specific Probes

RNA for the extracellular matrix glycoprotein fibronectin was localized in rat fibroblasts (RFL-6) and myoblasts (L6) using a 6.5 kb genomic probe derived from the gene sequence starting at about 6 kb from the transcription initiation site. The cells were grown and analyzed as monolayers on glass cover slips. Before hybridization, cells were treated three times (10–30 sec. each) with Hank's solution at room temperature, followed by a 10 sec wash with cytoskeleton buffer (CSK—100 mM NaCl, 300 mM sucrose, 10 mM PIPES, 3 mM $MgCl_2$, 1:20 vanadyl denosine complex) at 4° C. The cells were then permeabilized by treatment for 30 sec. with 0.5% Triton X-100 in CSK buffer at 4° C. and washed for 10 sec. with CSK buffer at 4° C. The permeabilized cells were fixed in 4% paraformaldehyde and 1× phosphate buffered saline (PBS) for 5 min. at room temperature. Cells were stored in 70% ethanol at 4° C. until hybridization.

The prepared cell samples were dehydrated on the slides by sequential exposure to 70%, 95% and 100% ethanol and air dried. The probe was dried, resuspended in 10 $\mu$l of 100% formamide and denatured at 75° C. for 10 min. Ten $\mu$l of hybridization buffer (2 parts 50% dextran sulfate, 1 part 20× saline sodium citrate (SSC), 1 part BSA and 1 part Vanadyl complex) was added to the denatured probe and mixed to give a final concentration of 5 $\mu$g/ml of probe. The probe solution was applied to the slides and incubated at 37° C. for 3–4 hr. After hybridization, the slides were rinsed according to the following protocol: two 30 min. washes in 2× SSC, 50% formamide at 37° C. and one 30 min. wash in the same buffer at room temperature. The hybridized cells were washed for 10 min. in 4× SSC prior to staining with fluorescein-avidin for 1 hr. with 1% BSA, 4× SSC. The stained cells were rinsed for 15 min. in 4× SSC, 15 min. in 4× SSC, 0.01% TRITON X-100, and 15 min. in 4× SSC, then observed under the fluorescence microscope.

Up to 80% of the nuclei showed one or two distinct sites of intense fluorescence, indicative of hybridization of the probe to accumulated fibronectin nuclear RNA. This result was confirmed by controls showing that the hybridization was specifically to RNA., as alkaline hydrolysis of RNA with NaOH removed the nuclear signals. The controls also confirm that the DNA of the corresponding gene was unavailable for hybridization with the RNA-specific probe during the RNA hybridization protocol.

It was observed that the fibronectin RNA frequently accumulated in tracks up to 6 $\mu$m long which, in some cells, extended through several planes of focus. The length and orientation of the tracks with respect to the x, y and z axes were variable. Similar, apparently non-specific orientation of tracks was observed in experiments to determine the nuclear localization of six different viral and cellular precursor mRNAs.

Similar in situ hybridizations to the transcripts from the inducible gene for neurotensin in rat PC-12 cells was accomplished using a genomic probe spanning the 10 kb gene. The cells were induced to express neurotensin by the addition of nerve growth factor (100 ng/ml), 1 $\mu$M dexamethasone, 1 $\mu$M forskolin (Sigma Chemical Co., St. Louis, Mo.) and 10 mM LiCl. Because the PC-12 cells have little cytoplasm and are nonadherent on glass, they did not require detergent treatment but instead were spun from suspension onto cover slips for 5 min. at 500 rpm and fixed in 4% paraformaldehyde for 5 to 10 min. Hybridization was performed essentially as described for fibronectin RNA. Approximately 4 hours after induction, 42% of positive cells showed one distinct focus of intense nuclear fluorescence and 58% showed two foci. A diffuse, less intense signal was often apparent throughout the cytoplasm and nucleoplasm. Elongated tracks were not observed. Neither the cytoplasmic or nuclear signals were detectable in uninduced PC-12 cells.

To determine whether the concentrated RNA signals detected with genomic probes represented unprocessed transcripts, mature mRNA or excised introns, in situ hybridization was performed with fibronectin intron-specific and exon-specific (cDNA) probes. The intron-specific probe was labeled with digoxigenin and detected with a rhodamine-conjugated antibody to digoxigenin. The cDNA probe was labeled with biotin and detected with FITC-avidin in the same cells hybridized with the intron-specific probe. Both probes hybridized to just one or two focal sites within the nuclear interior and the two-color labeling demonstrated that both probes hybridized to the same nuclear foci, indicating the presence of unspliced transcripts. Similar results were obtained in parallel experiments for neurotensin RNA.

EXAMPLE 2

Co-Localization of Fibronectin RNA Tracks and Fibronectin Gene

To determine whether RNA tracks and foci colocalized with the sites of transcription, hybridizations were performed to demonstrate the spatial relationship of the gene and the RNA. Fibronectin RNA was selected because of its more elongated track. This was accomplished by two-color simultaneous hybridization in situ to RFL-6 fibroblasts with a 4.3 kb digoxigenin-labeled probe for the nontranscribed 5' sequence immediately flanking the fibronectin gene (the DNA-specific probe) and a 6.5 kb biotin-16-dUTP-labeled probe for genomic DNA (the RNA-specific probe). The hybridized probes were detected by anti-digoxigenin antibody conjugated to rhodamine and avidin conjugated to FITC, respectively.

Both probes, plus 30–50 $\mu$g of $C_ot1$ DNA, were added to a tube and dried. Slides with cells prepared as in Example 1 were rinsed in 1× PBS to remove ethanol and then rinsed in 2× SSC. The cells were denatured in 70% formamide, 2× SSC at 70° C. for 2 min., then dehydrated sequentially in 70%, 95% and 100% ethanol. The prepared slides were air dried. The dried probe mixture was resuspended in 10 $\mu$l of 100% formamide and the probes denatured at 75° C. for 10 min. 10 $\mu$l of hybridization buffer was added to the probe and mixed. The probe solution was applied to the slides and incubated for about 3–4 hr. or overnight. After hybridization, the slides were rinsed 30 min. in 2× SSC, 50% formamide at 37° C., 30 min. in 2× SSC at 37° C. and 30 min. in 1× SSC at room temperature. After an additional wash for 10 min. in 4× SSC, the cells were stained for 1 hr. with rhodamine-conjugated anti-digoxigenin and fluorescein-conjugated avidin in 4× SSC, 1% BSA at 37° C.

Photomicrographs of the stained cells were taken through a dual-band filter that allows precise alignment of red and green fluorescence. Alternatively, the image was captured by a charge coupled device (CCD) camera from separate filters superimposed and aligned with multicolor fluorescence beads as fiduciary markers.

The gene and the RNA were found to be spatially coincident. For 86% of the gene signals detected there was an overlap between the signals from the gene and the RNA track. Furthermore, in 88% of the RNA tracks the gene was clearly positioned at or near one end. This polarity was apparent even within focal (non-elongated) accumulations of fibronectin RNA. These results show that RNA foci and tracks form directly at the site of transcription and indicate a structural polarity to RNA formation with the gene toward one end. Because the length of the gene is below the resolution of the light microscope the gene signal is seen as a point of fluorescence. For this reason the longer RNA formations observed are not equivalent to the "Christmas tree" of nascent transcripts synthesized along the DNA template as has been identified by electron microscopy for *Drosophila melanogaster* ribosomal DNA and the transcripts of amplified chorion genes, but instead appear as accumulations of many RNA molecules that extend well beyond the dimensions of the gene.

Different hypotheses could explain RNA accumulation at the site of transcription. For example, it could represent a buildup of newly synthesized transcripts before transport elsewhere for processing or it could represent an "assembly line" of transcripts that undergo processing at or near the transcription site. Further two-color simultaneous hybridization studies with fibronectin cDNA and intron probes (cohybridization protocol) which allowed precise registration of the two colors demonstrated that the "assembly line" hypothesis is likely to be correct. In 85% of cells, hybridization with a digoxigenin-labeled cDNA probe (detected with anti-digoxigenin-rhodamine) formed longer tracks than those detected with a biotinylated intron-specific probe (detected with avidin-FITC). Within a single cell, the intron signal was generally confined to a smaller part of the track than the exon signal, creating the appearance of a two-color, segmented track. The segmented track was consistently observed with two different analytical methods: 1) a single filter set that allowed simultaneous visualization of red and green with no optical shift (Chroma Technology, Brattleboro, VT; C. V. Johnson, et al. (1991), supra; D. C. Tkechuk, et al. *Science* 250:559 (1990)), and 2) separate images captured by a cooled charge coupled device (CCD) camera that were aligned and superimposed. In control experiments in which a single probe was labeled with two colors, there was no separation of the red and green signals. The absence of intron sequences from a portion of the focus or track defined by the cDNA probe indicates that intron splicing occurs within the accumulation of RNA. Further, the results indicate that the splicing process is spatially ordered within the RNA track and that the RNA transcripts are physically associated with a nuclear substructure. It was also observed with both genomic and intron probes that a less intense fluorescence was dispersed throughout the nucleoplasm, excluding the nucleolus, indicating that excised intron sequences apparently diffuse freely.

EXAMPLE 3

Fibronectin Transcript Domains

The distribution of fibronectin RNA relative to the transcript domains previously reported was investigated. Two different overlapping probes were used to define the transcript domains (K. C. Carter, et al. (1993), supra; K. C. Carter, et al. (1991), supra): oligo(dT) to detect total poly(A) RNA and an antibody to the spliceosome assembly factor SC-353 (X. D. Fu and T. Maniatis, Nature 343:437 (1990)). A 2 kb digoxigenin-labeled cDNA probe for fibronectin RNA, detected using anti-digoxigenin-FITC, was hybridized first as described above. The biotinylated oligo(dT) probe (0.5 μg/ml) was then hybridized in 15% formamide and 2× SSC at 37° C. for 3 hr. and detected using rhodamine-avidin.

Quantitative analysis of >100 cells by direct microscopic visualization through a dual-band filter or by superimposed computer images of optically sectioned cells captured from a CCD camera showed a nonrandom spatial relationship between fibronectin RNA foci or tracks and the larger transcript domains rich in poly(A) RNA and SC-35. Analysis was performed with optics that allow 0.5 μm z-axis resolution (Zeiss Neufluor 100, 1.4 numerical aperture). Approximately 88% of fibronectin RNA tracks or foci were associated with poly(A) RNA-rich transcript domains, with the majority (80%) either overlapping or in contact with the domain. Only about 8% of the tracks were completely within the domain and about 12% were not in contact. As the nuclear volume occupied by all of other poly(A) domains in a given nucleus is estimated to be about 5% and specific RNA accumulations no more than about 1%, the frequency with which fibronectin RNA would spatially associate with these domains by random chance is small. The association of fibronectin RNA with the transcript domains therefore appears to be highly specific. The specificity of the association is further demonstrated by previous experiments showing that nontranscribed centromeric sequences are not associated with poly(A) containing domains.

The number, relative size and intensity of the signals for poly(A) RNA domains versus the signals for the specific RNA suggest that each transcript domain reflects the transcription and processing activity of several different genes. This is because the poly(A) RNA was detected with a small (55 nt) oligonucleotide end-labeled with only a few biotin molecules, whereas the fibronectin RNA is detected by much larger (1–6 kb) probes labeled throughout by nick translation. The amount of fluorescence generated per molecule with the poly(A) probe is therefore expected to be at least an order of magnitude less than that generated by the fibronectin mRNA probe. However, estimations of the relative intensity and size of individual poly(A) RNA domains indicated that the domains contain substantially more fluorescent signal than individual RNA foci or tracks do. This consideration, along with the other observation that fibronectin RNA tracks only partially overlap the transcript domains, supports the conclusion that each transcript domain is likely to be the transcription and processing site of several RNAs.

The monoclonal antibody to SC-35 was allowed to bind at 37° C. for 60 min. and then detected using a rhodamine-conjugated donkey antibody to murine immunoglobulin (Jackson ImmunoResearch Labs.). The pattern of colocalization was similar for Sc-35, but the fraction of fibronectin RNA tracks not in contact or overlapping a visible transcript domain increased to 32%, with 68% in contact with the domain. This is consistent with the observation that SC-35 forms a smaller inner core in the domain, so that some tracks may overlap the periphery of poly(A) domains without contacting the SC-35 core. Optical sectioning of several cells in 0.2 μm optical steps indicated that the fibronectin RNA accumulations did not extend to the nuclear envelope but were within the nuclear interior.

EXAMPLE 4

Detection of Transgene Expression

Fluorescence in situ hybridization according to the invention was used to detect expression of multiple copies of the M. spretus collagen gene in transgenic mouse cells, associated with an integrated pYAC151 vector. First, fluorescence in situ hybridization to genomic DNA was used to confirm that the transgene was carried at a single chromosome location. The digoxygenin labeled Col1a1 probe (detected with rhodamine) generated a single hybridization signal in the parental cells which was also seen in the transfected clones. The signal corresponded to the endogenous Col1a1 gene on chromosome 11. A second collagen specific hybridization signal, which was also labeled by the vector probe, was seen in each of the transfected cell lines but not in the parental cells. The signal was localized close to the centromere of a large chromosome in one clone and close to the telomere of a smaller chromosome in another clone. The vector and donor Col1a1 sequences therefore colocalize to a unique chromosomal site in the two transfected cell clones and together with Southern blot analyses, are consistent with each transgene being physically intact.

To demonstrate expression of the YAC transgene, primary dermal fibroblasts were prepared from control and transgenic animals and assayed for expression of α1 (I) collagen using fluorescent in situ hybridization. Four cell samples were isolated and hybridized to an RNA-specific nucleotide probe (the genomic probe) as described in Example 1 for hybridization to RNA but not DNA. In control cells, 78% of the population showed two large foci or tracks of nuclear RNA, indicating two sites of transcription. Only 5% showed three tracks. In contrast, analysis of cells from transgenic animals demonstrated that in the majority of cells (61–66%) there were three easily detectable collagen RNA tracks, demonstrating that collagen RNA was being produced at three distinct sites, corresponding to the three copies of the gene.

Confirmation that the third nuclear RNA signal was produced from the transgene sequence was achieved by simultaneous hybridization of collagen nuclear RNA and the 11 kb YAC vector DNA. Fibroblast cells from transgenic animals were simultaneously hybridized (sequential hybridization protocol) with a 24 kb genomic probe corresponding to the Col1a1 collagen gene (detected by fluorescein-avidin) and to an 11 kb probe corresponding to the pYAC151 vector (detected by anti-digoxygenin-rhodamine). RNA-specific hybridization to the genomic probe was performed as in Example 1 but instead of observing the stained slides after the final rinse in 4× SSC, the cells were fixed a second time in 4% paraformaldehyde for 10–15 min. at room temperature. The fixed cells were rinsed in 1× PBS for 10 min. followed by a 10 min. wash in 2× SSC. The DNA-specific YAC probe was dried, resuspended and denatured in the same way as the RNA-specific probe in Example 1. The nucleic acids in the prepared cells were denatured in 70% formamide, 2× SSC at 70° C. for 2 min., dehydrated sequentially in 70%, 95% and 100% ethanol, and air dried. The probe solution was applied to the slides and incubated at 37° C. overnight. Following hybridization, the slides were rinsed and stained as described in Example 1 using anti-digoxygenin-rhodamine for detection of DNA. The slides were then mounted in anti-bleach mounting medium (Pheneyline dimine, Sigma Chemical Co., St. Louis, Mo.) and observed under the fluorescence microscope.

In cells from transgenic animals only, one collagen RNA track (labeled with fluorescein) was tightly spatially associated with DNA from the YAC transgene vector (labeled with rhodamine). This association was observed in over 95% of cells and demonstrated that the RNA track was correlated with expression of the transgene. No vector sequences were detected in the control. It was also observed that when a larger RNA track was present (in about 48% of cells analyzed) it showed significant correlation with expression of the transgene rather than the endogenous gene (96% of cells). These results demonstrate that not only is the collagen transgene expressed, it is expressed at a level which is equivalent to or greater than the endogenous sequences. Using the present in situ hybridization methods for detecting transcription of specific, selected genes, the level of expression of the gene can also be determined by quantitating the level of fluorescence associated with the RNA track or focus.

EXAMPLE 5

Specific Detection of Defective Splice in collagen Iα1 RNA

The distribution of collagen Iα1 transcripts was investigated in mutant fibroblast cells (054) from a patient with Nondeforming (Type 1) osteogenesis imperfecta, using in situ hybridization. The patient was heterozygous for the collagen Iα1 gene, carrying a dominant mutant allele in which there was a G→A transition at the +1 donor position of intron 26. The point mutation resulted in retention of exon 26, and failure of the mutant transcripts to be transported to the cytoplasm.

Cell Culture and Cell Fixation

Cultured human diploid fibroblast lung cells, WI-38 (American Type Culture Collection, Rockville, Md., Catalog No. CCL 75) were used as normal control cells for comparison with the 054 cells. The WI-38 cells were grown in Dulbecco's Modified Eagle's medium, high glucose (DMEM-high), with 10% fetal calf serum (FCS) (GIBCO BRL, Gaithersburg, Md.) and penicillin-streptomycin added. The 054 patient cells were grown in DMEM, 10% FCS, non-essential amino acids, glutamine, and penicillin-streptomycin. In some instances, the FCS concentration was raised from 10% to 20%, to improve cell growth.

Prior to fixation, the mutant cells and control cells were washed in cytoskeletal (CSK) buffer (100 mM NaCl, 300 mM sucrose, 3 mM MgCl2, 10 mM Pipes, pH 6.8; Fey et al., 1986) and incubated for 5 minutes on ice in CSK containing 5% Triton X-100 and 2 mM vanadyl ribonucleoside complex (VRC; GIBCO BRL). Cells were next quickly fixed for 8 minute in 4% papaformaldehyde-1X PBS (pH 7.4). Cells were stored in 70% ETOH at 4° C.

Probes and Antibodies

A genomic, 40-kb cosmid clone containing the entire 18-kb Human Collagen Iα1 gene (CG103), was obtained (see Barsh et al., "DNA and Chromatin Structure of the Human α1(I) Collagen Gene," *J. Biol. Chem.* 259:14906–14913 (1984)). A human collagen Iα1 cDNA (1.8 kb insert) is available from the American Type Culture Collection (ATCC catalog no. 61322 or 61323). Human collagen Iα1 intron 26-specific probes were generated by PCR amplification of intron 26 sequences only.

SC-35 domains were detected by immunofluorescence using a mouse monoclonal antibody against the spliceosome assembly factor SC-35, provided by Dr. T. Maniatis (Harvard University, Cambridge, Mass.). Anti-SC-35 antibody reacts with a non-snRNP spliceosome assembly factor and may detect another structural protein which colocalizes to the same nuclear domains. Anti-SC-35 antibodies are described in Fu et al., *Nature* 343:437–444 (1990).

Fluorescence in situ Hybridization and Immunofluorescence Staining

Probes for hybridization were nick translated using digoxigenin 11-dUTP or biotin 16-dUTP. For RNA hybridizations, cells were removed from storage in 70% ETOH, dehydrated in 100% EtOH for 5 minutes and allowed to air dry. Labeled probe (50 ng) per sample was lyophilized with 10 ug each of salmon sperm DNA, *E. Coli* tRNA, and human Cot 1 DNA and resuspended in 10 ul of 100% formamide. The probe was heat denatured for 10 minutes at 70° C. for 10 minutes prior to the addition of an equal volume of hybridization buffer (2 parts 50% dextran sulfate, 1 part 20× SSC, 1 part BSA, and 1 part vanadyl complex), which was then applied to the dried cells. Cells were incubated at 37° C. for a period of 3 to about 18 hours.

To compare the intracellular distribution of collagen Iα1 transcripts in 054 cells and in WI-38 control cells, in situ hybridization was carried out using genomic probes, cDNA probes, and intron specific probes, alone, in combination with each other, or in combination with an antibody against the spliceosome assembly factor SC-35. Collagen RNA in cell lines from patients with a collagen Iα1 gene mutation that created an in frame stop codon were also examined by fluorescence in situ hybridization. Transcripts from this mutant allele also fail to be transported to the cytoplasm. The nuclear distribution was analyzed with respect to SC35 domains and its proximity to the nuclear envelope.

A probe specific for intron 26 was used in an in situ hybridization experiment to examine the distribution of intron 26 in transcripts from the normal and mutant collagen Iα1 allele in 054 cells and WI-38 control cells. The intron 26-specific probe was nick translated with digoxigenin 11-dUTP to provide a ligand for specific binding of a receptor bearing a covalently attached fluorochrome.

In WI-38 cells subjected to in situ hybridization, the signal from the intron-specific probe appeared as a small focus, generally at one end of the larger focus of RNA detected with a cDNA or genomic probe (FIGS. 1A–1C). Generally, there was a significant fraction of cells with in situ hybridization signals from both alleles. When signals were detected from both alleles in WI-38 cells, the accumulations appeared to be similar in size and intensity (FIG. 1B). Occasionally, a signal from an intron 26 probe was larger than a pinpoint, but never as large as the signal generated from a cDNA or genomic probe.

When 054 cells were hybridized with an intronspecific digoxigenin labeled probe, intron 26 gave a less uniform signal from allele to allele. The most striking result was the presence of a signal focus much larger than the signal in the WI-38 control cells (FIGS. 1D–1F).

A double label in situ hybridization experiment using an intron 26-specific probe labeled with digoxigenin, and a collagen Iα1 cDNA (1.8 kb fragment) labeled with biotin, provided a reference for the extent of overlap between intron and cDNA signals. In WI-38 cells, the intron signal overlapped only a portion of the area covered by the cDNA signal, and it was generally at one end of the large cDNA focus (FIGS. 1A–1C). At one allele in 054 cells, intron 26 completely overlapped the cDNA signal, while at the other allele, RNA accumulation appeared similar to that in the WI-38 control cells (FIGS. 2D–2F).

We have studied the distribution of several genes/transcripts relative to SC35 domains, which are discrete regions in the nucleus rich in splicing factors. Thus far, no inactive genes have been found associated with SC35 domains. However, many, but not all, active genes and transcripts are associated with SC35 domains. The degree of association can be as high as 100%. Not all transcripts associate with SC35 in a similar manner. Collagen RNA completely enters SC-35 domains, while other RNAs, such as fibronectin RNA, associate with the edges of SC-35 domains. The collagen gene displays a polar distribution relative to collagen transcripts. The collagen gene sits at the edge of an SC-35 domain and its RNA enters the domain. Thus, transcription occurs at the border of these domains and the RNA enters from the site of transcription.

Intron 26 in WI-38 cells is spliced at the domain periphery, and the spliced RNA then enters the domain. In the mutant cells, in which intron 26 is not spliced from the collagen transcript, the RNA still enters the domain. Hence, the defectively spliced RNA can be detected by a concentration of intron-containing RNA throughout the SC-35 domain, instead of only at the SC-35 domain's edge.

Other embodiments are within the following claims.

We claim:

1. An in situ hybridization method for detecting normal splicing, if present, of RNA transcribed from a gene of interest in a cell, said method comprising the steps of:
   (a) fixing said cell with a fixative such that the nucleus remains penetrable by labeled probes, and the nucleic acids are preserved in place;
   (b) hybridizing said fixed cell with an intron-specific nucleic acid probe able to hybridize to an intron of interest encoded by a gene of interest, said intron-specific probe bearing a first label;
   (c) hybridizing said fixed cell with an exon-specific nucleic acid probe able to hybridize to at least one exon in said gene of interest, said exon-specific probe bearing a second label, said second label being distinguishable from said first label;
   (d) detecting said second label as a large focus or track; and
   (e) detecting said first label as a small focus or track within said large focus or track, said small focus or track having a size and shape such that it does not substantially totally overlap said large focus or track, as an indication of normal splicing of RNA transcribed from said gene of interest in said cell.

2. The method of claim 1, further comprising, as an initial step, permeabilizing the nucleus of said cell while minimizing mRNA degradation.

3. The method of claim 1, wherein said first label and said second label are different fluorochromes whose emission wavelengths are clearly distinguishable.

4. An in situ hybridization method for detecting defective splicing, if present, of RNA transcribed from a gene of interest in a cell, said method comprising the steps of:
   (a) fixing said cell with a fixative such that the nucleus remains penetrable by labeled probes, and the nucleic acids are preserved in place;
   (b) hybridizing said fixed cell with an intron-specific nucleic acid probe able to hybridize to an intron of interest encoded by a gene of interest, said intron-specific probe bearing a detectable label;
   (c) detecting said label as a large focus, as an indication of defective splicing of RNA transcribed from said gene of interest in said cell.

5. The method of claim 4, further comprising, as an initial step, permeabilizing the nucleus of said cell while minimizing mRNA degradation.

6. The method of claim 4, wherein said label is a fluorochrome.

7. An in situ hybridization method for detecting defective splicing, if present, of RNA transcribed from a gene of interest in a cell, said method comprising the steps of:
   (a) fixing said cell with a fixative such that the nucleus remains penetrable by labeled probes, and the nucleic acids are preserved in place;
   (b) hybridizing said fixed cell with an intron-specific nucleic acid probe able to hybridize to an intron of interest encoded by a gene of interest, said intron-specific probe bearing a first label;
   (c) hybridizing said fixed cell with an exon-specific nucleic acid probe able to hybridize to at least one exon in said gene of interest, said exon-specific probe bearing a second label, said second label being distinguishable from said first label;
   (d) detecting said second label as a signal focus that substantially completely overlaps a signal focus from said first label, as an indication of defective splicing of RNA transcribed from said gene of interest in said cell.

8. The method of claim 7, further comprising, as an initial step, permeabilizing the nucleus of said cell while minimizing mRNA degradation.

9. The method of claim 7, wherein said first label and said second label are different fluorochromes whose emission wavelengths are clearly distinguishable.

10. The method of claim 7, wherein steps (b) and (c) are performed simultaneously by having said intron-specific probe and said exon-specific probe present in a single hybridization reaction.

11. An in situ hybridization method for detecting defective splicing, if present, of RNA transcribed from a gene of interest in a cell, said method comprising the steps of:
    (a) fixing said cell with a fixative such that the nucleus remains penetrable by labeled probes, and the nucleic acids are preserved in place;
    (b) subjecting said fixed cell to an in situ hybridization reaction comprising:
        (1) a labeled, full-length genomic probe comprising the antisense sequence of an entire gene of interest, said full-length genomic probe bearing a label, and said full-length genomic probe being present in said hybridization reaction at a concentration between 0.5 $\mu$g/ml and 20 $\mu$g/ml; and
        (2) an unlabeled full-length cDNA probe comprising the complete coding region of said gene of interest, said cDNA probe being present in said hybridization reaction at a concentration between 50-fold greater and 500-fold greater than the concentration of said labeled genomic probe; and
    (c) detecting said label as a large focus in the nucleus of said cell, as an indication of defective splicing in RNA transcribed from said gene of interest in said cell.

12. The method of claim 11, further comprising, as an initial step, permeabilizing the nucleus of said cell while minimizing mRNA degradation.

13. The method of claim 11, wherein said label is a fluorochrome.

14. An in situ hybridization method for detecting defective splicing, if present, of RNA transcribed from a gene of interest in a cell, said method comprising the steps of:
    (a) fixing said cell with a fixative such that the nucleus remains penetrable by labeled probes, and the nucleic acids are preserved in place;

(b) hybridizing said fixed cell with a cDNA bearing a first label;

(c) fixing said cell to preserve in place the hybridized cDNA of step (b);

(d) hybridizing said fixed cell with a full-length genomic probe comprising the antisense sequence of an entire gene of interest, said full-length genomic probe bearing a second label, said second label being distinguishable from said first label;

(e) detecting said second label as a focus that substantially completely overlaps a signal focus from said first label, as an indication of a defective splicing of RNA transcribed from said gene of interest in said cell.

15. The method of claim 14, further comprising, as an initial step, permeabilizing the nucleus of said cell while minimizing mRNA degradation.

16. The method of claim 14, wherein said first label and said second label are different fluorochromes whose emission wavelengths are clearly distinguishable.

* * * * *